United States Patent
Fan et al.

[11] Patent Number: 5,900,472
[45] Date of Patent: May 4, 1999

[54] COPOLYMERIZABLE BENZOPHENONE PHOTOINITIATORS

[75] Inventors: Mingxin Fan, West Chester; Gary W. Ceska, Exton; James Horgan, West Chester, all of Pa.

[73] Assignee: Sartomer Technology, Exton, Pa.

[21] Appl. No.: 08/772,432

[22] Filed: Dec. 23, 1996

[51] Int. Cl.[6] .............................. C08G 6/00; C08G 10/00; C08G 14/00
[52] U.S. Cl. .................... 528/220; 528/125; 528/129; 528/271; 430/56; 430/127; 430/135; 427/54.1; 427/508; 428/436; 428/442
[58] Field of Search .................... 528/125, 129, 528/220, 271; 430/56, 127, 135; 427/508, 54.1; 428/436, 442

[56] References Cited

U.S. PATENT DOCUMENTS 4,180,599  12/1979  Wolpert et al. ..................... 427/54.1

*Primary Examiner*—Duc Truong
*Attorney, Agent, or Firm*—Michael B. Fein; Schnader Harrison Segal & Lewis, LLP

[57] ABSTRACT

Copolymerizable benzophenone photoinitiators of the formula I

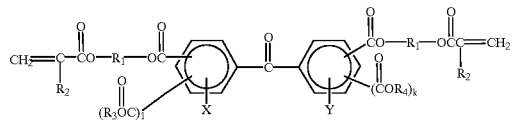

wherein 1, k=0, 1, 2.
$R_1$=divalent organic group having 1 to 25 carbon atoms;
$R_2$=H or methyl; and
$R_3$, $R_4$=organic group having 1 to 25 carbon atoms.
X, Y=hydrogen, halogen or ($C_1$–$C_{25}$) groups containing N, S, and/or O;

and method of making the photoinitiators.

The photoinitiators overcome the leaching problem with prior photoinitiators in radiation curable polymer applications. Radiation curable polymers, cured polymers, and coated articles are also disclosed.

11 Claims, No Drawings

COPOLYMERIZABLE BENZOPHENONE PHOTOINITIATORS

BACKGROUND OF THE INVENTION

1. Field of the Invention

This invention relates to benzophenone photoinitiators useful in UV curable coating compositions.

2. Description of the Prior Art

Prior benzophenone photoinitiators used in UV curable coating compositions suffered from being leachable because only a fraction of the photoinitiator is consumed during the UV curing process. The large portion of benzophenone which was not consumed remained present in the polymer matrix as a free component, and was leachable upon contact with various liquids, or tended to migrate to the coating surface over time.

Prior attempts to solve the leaching problem with benzophenone photoinitiators in UV curable coating compositions involved incorporating benzophenone into the polyester backbone. U.S. Pat. No. 4,022,674 shows benzophenones with multiple carboxylic acid functionality which react with amine coinitiator. Also, various benzophenone monofunctional (meth)acrylates were synthesized, but they are not practical and not successful because high extractable levels still exist with such photoinitiators. None of the prior attempts to solve this problem have been adequate.

Prior art benzophenones having more than one reactive group had only acid functionality and were suitable for reacting with hydroxyl-functional monomers so as to form polyester linkages. Such linkages are not suitable in UV curable coating systems in which amine coinitiators are present to enhance surface cure.

SUMMARY OF THE INVENTION

It is an object of this invention to provide benzophenone photoinitiators which are useful in UV curable coating compositions which do not suffer from the leaching problem.

This object, and others which will become apparent from the following disclosure, are achieved by the present invention which comprises in one aspect benzophenone compounds having two to four (meth)acrylate groups of the formula

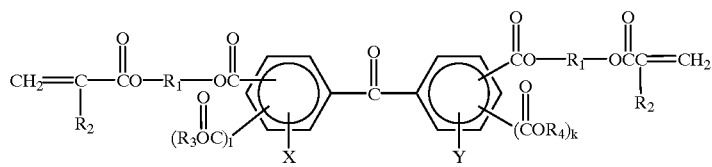

(I)

wherein l, k=0, 1, 2.

$R_1$=divalent organic group having 1 to 25 carbon atoms;

$R_2$=H or methyl; and $R_3$, $R_4$=organic group having 1 to 25 carbon atoms.

X, Y=hydrogen, halogen or ($C_1$–$C_{25}$) groups containing N, S, and/or O.

In another aspect the invention comprises a method of preparing UV curable coating compositions comprising mixing a benzophenone compound of formula I with "(meth)acrylate", i.e., acrylate, methacrylate, or mixtures thereof, monomer, and applying UV light or electron beam radiation to cure the coating composition.

The improved articles comprising the cured polymers are another aspect of the invention.

DETAILED DESCRIPTION OF THE INVENTION AND THE PREFERRED EMBODIMENTS

The benzophenone compounds of formula I are prepared by reacting a benzophenone dianhydride of formula II

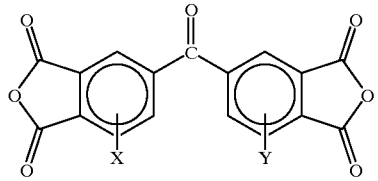

(II)

or acid derivatives of formula III

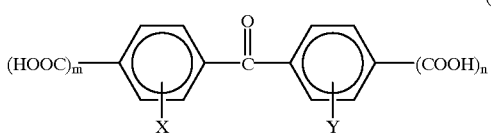

(III)

wherein n, m=1,2,3 integer and the sum of n+m is in the range of 2–6; with a compound of formula IV

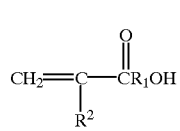

(IV)

wherein $R_1$=divalent organic group having 1 to 25 carbon atoms; and $R_2$=H or methyl; followed by reacting with alcohol or monoepoxide.

Suitable benzophenone compounds of formula II or III include: 3, 4, 3', 4'-benzophenonetetracarboxylic acid dianhydride, benzophenonetetracarboxyl acid, benzophenonedicarboxylic acid, benzophenonetricarboxylic acid, benzophenonepentacarboxyl acid, benzophenonehexacarboxyl acid. Other compounds of formula II or III can be used but are not readily available.

Suitable compounds of formula IV include hydroxyethyl acrylate, hydroxyethyl methacrylate, hydroxybutyl acrylate, 2-hydroxypropyl (meth)acrylate, hydroxypolycaprolactone (meth)acrylate, and acrylates and methacrylates where $R_1$ is alkoxy, including ethoxy and propoxy.

Suitable alcohols include methyl alcohol, ethyl alcohol, propyl alcohol, butanol, octanol, alphaterpineol, geranial, cinnanyl alcohol, decyl alcohol, heptenol, cholesterol, and the like.

Suitable monoepoxides include glycidyl ester of neodecanoic acid, 2-ethylhexyl glycidyl ether, P-ter-butylphenyl glycidyl ether, nonylphenyl glycidyl ether, phenyl glycidyl ether, cresyl glycidyl ether, butyl glycidyl ether, alkyl ($C_8$–$C_{20}$) glycidyl ethers, epoxidized alpha olefins.

The dianhydrides of formula II or acids of formula III can be reacted with compounds of formula IV, preferably under atmospheric pressure at about 10–150° C., in a 1:2–1:6 ratio.

The more preferred reaction temperature is 80–120° C. and the more preferred reactant ratio is 1:2–1:4.

The radiation curable compositions comprise (meth) acrylate monomers such as methyl methacrylate, methyl acrylate, multifunctional monomers, and olgomers. Coinitiators such as amines, for example dimethyl ethanolamine or acrylated amines, can also be included.

The benzophenone photoinitiators of the invention are included in the radiation curable composition in a concentration of about 0.01–50% by weight.

The benzophenones of the invention have two to six copolymerizable (meth)acrylate groups which allows them to act as a combination monomer and photoinitiator in radiation curable compositions in which the benzophenone molecule becomes part of the network bonded to the matrix, thereby reducing migratables and extractables.

Another advantage to use of the benzophenone compounds of the invention is improved surface cure of radiation cured compositions, especially in UV curable coatings embodiments.

The following examples present a few embodiments of the invention.

EXAMPLES

Example 1

3,3', 4,4'-Benzophenonetetracarboxylic dianhydride (BTDA, 125.0 g), hydroxyethylmethacrylate (125.0 g), 4-methoxyphenol (0.15 g), and dimethylethanolamine (0.5 g) were stirred and heated to 120° while air sparge was applied. The mixture became clear in 15 min. and reacted for 2.0 hrs. at 120° C., followed by slow addition of cresyl glycidyl ether (151.0 g). The addition was completed in 30 min. and the reaction mixture was kept at 120° C. for an additional 5.0 hrs. The final product was very viscous with epoxy value of 9.16 mg KOH/g and acid value of 4.41 mg KOG/g.

Example 2

Example 1 was repeated using alkyl ($C_{12}$–$C_{14}$) glycidyl ether (187.0 g) instead of cresyl glycidyl ether.

Example 3

3,3', 4,4'-Benzophenonetetracarboxylic dianhydride (80.6 g), hydroxyethyl acrylate (58.0 g), 4-methoxyphenol (0.40 g), dimethylethanol amine (0.5 g), and hexanediol diacrylate (35.0 g, as solvent) were reacted at 110° C. with mechanical stirring and air sparge. Then alkyl ($C_{12}$–$C_{14}$) glycidyl ether (126.4 g) and benzyltriethyl ammonium chloride (1.50 g) were added, then the reaction mixture was stirred at 110° C. for 2.5 hrs. A dark brown resin was obtained with viscosity (25° C.):7940 cps; color: G-12; AV=3.79 mg KOH/g and EV=2.18 mg KOH/g.

Example 4—Comparative

For comparison, a monofunctional methacrylate benzophenone was prepared. 2-benzoylbenzoic acid (113.2 g) and 4-methoxyphenol (0.06 g) were heated to 130° C. in a three-neck flask to melt, then air sparge was applied and glycidyl methacrylate (77.5 g) and benzyltriethylammonium chloride (0.20 g) were added under stirring. The reaction mixture was stirred at 120° C. for 2½ hrs. A viscous resin was obtained.

Example 5—UV Curable Compositions Using Benzophenone Photoinitiators.

A number of formulations were made to test the photoinitiators and its effectiveness relative to commercial UVecryl P36 and benzophenone itself. The formulations were cured using one 600 watt/inch Fusion H lamp at full power in air at minimum lamp height on Form2A Leneta charts.

TABLE 1

| CN384 | KIP-100F | BZP | P36 | A | B | max. surf. finger nail | line speed fpm | film odor | 60 deg gloss | MEK double Rubs |
|---|---|---|---|---|---|---|---|---|---|---|
| 6.33 | 1 | 0 | 2.67 | 0 | 0 | 140 | 100 | Slight | 91.2 | 40 |
| 0 | 5 | 0 | 5 | 0 | 0 | 340 | 100 | Slight | 98 | 70 |
| 6.33 | 1 | 0 | 0 | 2.67 | 0 | 80 | 80 | Medium | 91.8 | 40 |
| 0 | 5 | 0 | 0 | 5 | 0 | 300 | 100 | None | 95.2 | 45 |
| 6.33 | 1 | 0 | 0 | 0 | 2.67 | 80 | 80 | Slight | 91.1 | 24 |
| 0 | 5 | 0 | 0 | 0 | 5 | 260 | 100 | Slight | 91.9 | 35 |
| 0 | 0.6 | 0.2 | 0 | 0 | 0 | <30 | 2X30 | Slight | 92.3 | 100+ |
| 0 | 0.6 | 0.4 | 0 | 0 | 0 | <30 | 2X30 | Slight | 90.4 | 28 |
| 0 | 0.6 | 0.6 | 0 | 0 | 0 | 40 | 40 | Slight | 95.3 | 90 |
| 0 | 0.6 | 0 | 0.2 | 0 | 0 | <30 | 2X30 | Slight | 91.4 | 24 |
| 0 | 0.6 | 0 | 0.4 | 0 | 0 | 30 | 30 | Slight | 93.7 | 100+ |
| 0 | 0.6 | 0 | 0.6 | 0 | 0 | 40 | 40 | Slight | 92.8 | 100+ |
| 0 | 0.6 | 0 | 0 | 0.2 | 0 | <30 | 2X30 | Slight | 90.7 | 100+ |
| 0 | 0.6 | 0 | 0 | 0.4 | 0 | <30 | 2X30 | Slight | 93.2 | 100+ |
| 0 | 0.6 | 0 | 0 | 0.6 | 0 | <30 | 2X30 | Slight | 94.4 | 100+ |
| 0 | 0.6 | 0 | 0 | 0 | 0.2 | <30 | 2X30 | Slight | 93.4 | 80 |

TABLE 1-continued

| CN384 | KIP-100F | BZP | P36 | A | B | max. surf. finger nail | line speed fpm | film odor | 60 deg gloss | MEK double Rubs |
|---|---|---|---|---|---|---|---|---|---|---|
| 0 | 0.6 | 0 | 0 | 0 | 0.4 | <30 | 2X30 | Slight | 94 | 100+ |
| 0 | 0.6 | 0 | 0 | 0 | 0.6 | <30 | 2X30 | Slight | 86.8 | 100+ |

Notes:
1) CN120A75, SR306, SK9020, SK399 are commercial acrylate monomers available from Sartomer Co.
2) DC57 is a commercial additive available from B&K Chemie.
3) B&K 301 is a commercial additive available from B&K Chemie.
4) CN384 is an acrylated amine available from Sartomer Co.
5) KIP-100F is a photoinitiator available from Sartomer Co.
6) P36 is Uveroyl P36, available from UCB Radcure.
7) BZP is benzophenone.
8) A is the photoinitiator from Example 2.
9) B is the photoinitiator from Example 1.

Based on the results shown in the above table, these new benzophenone photoinitiators are much better than benzophenone itself and behave similarly to commercial monofunctional analogues.

While the invention has been described in detail herein, various alternative embodiments and improvements should become apparent to those skilled in the art without departing from the spirit and scope of the intention as set forth in the following claims.

What is claimed is:

1. Dimethacrylate compound of the formula:

$$CH_2=C(R_2)-CO-R_1-OC-\underset{(R_3OC)_l}{\underbrace{\phantom{XXX}}_{X}}-C(=O)-\underset{(COR_4)_k}{\underbrace{\phantom{XXX}}_{Y}}-CO-R_1-OCC(R_2)=CH_2 \quad (I)$$

wherein
   l, k=1;
   $R_1$=divalent organic group having 1 to 25 carbon atoms;
   $R_2$=H or methyl;
   $R_3$, $R_4$=organic group having 1 to 25 carbon atoms other than acrylate, methacrylate, or carbonyl; and
   X, Y=hydrogen, halogen, or ($C_1$–$C_{25}$) groups containing N, S, and/or O.

2. Compound according to claim 1 wherein $R_3$, $R_4$ are residues of an alkyl glycidyl ether or an aryl glycidyl ether.

3. Compound according to claim 1 wherein $R_1$=($C_2$–$C_6$) alkylene and $R_3$ and $R_4$ are each selected from the group consisting of $$CH_3C_6H_4OCH_2CH(OH)CH_2-$$

$$(C_{12}\text{-}C_{14})alkyl\text{-}OCH_2CH(OH)CH_2-.$$

4. A method of using a compound in accordance with claim 1 comprising mixing 0.1–50% by weight with one or more radiation curable monomers to form a radiation curable composition, and applying radiation to the surface so as to cure the composition.

5. Radiation-cured polymer composition comprising moieties derived from a compound according to claim 1.

6. Method of making compounds in accordance with claim 1 comprising reacting a benzophenone dianhydride of the formula (II)

(benzophenone dianhydride structure, formula II)

(HOOC)$_m$—Ar—C(=O)—Ar—(COOh)$_m$ with substituents X and Y with a compound of formula IV $$CH_2=C(R^2)-C(=O)-CR_1OH \quad (IV)$$

wherein
   $R_1$=divalent organic group having 1 to 25 carbon atoms; and
   $R_2$=H or methyl;
followed by reacting with an allyl or aryl monoepoxide to form a di(meth)acrylate compound of Formula I.

7. Method of claim 6 wherein compound IV is selected from hydroxyethyl acrylate, hydroxyethyl methacrylate, hydroxybutyl acrylate, 2-hydroxypropyl (meth)acrylate, hydroxypolycaprolactone (meth)acrylate, and acrylates and methacrylates where $R_1$ is alkoxy.

8. Radiation curable composition comprising a photoinitiator compound according to claim 1 and one or more other methacrylate or acrylate monomers.

9. Radiation cured coating prepared by curing a composition according to claim 8.

10. Articles having a surface coated with a composition according to claim 9.

11. Method according to claim 6 wherein said glycidyl compound is selected from the group consisting of ($C_{12}$–$C_{14}$)alkyl glycidyl ether and methylphenyl glycidyl ether.

* * * * *

UNITED STATES PATENT AND TRADEMARK OFFICE
CERTIFICATE OF CORRECTION

PATENT NO.: 5,900,472
DATED: May 4, 1999
INVENTOR(S): Fan et al

It is certified that error appears in the above-identified patent and that said Letters Patent is hereby corrected as shown below:

In column 5, at approximately line 55, under claim 3, please change:

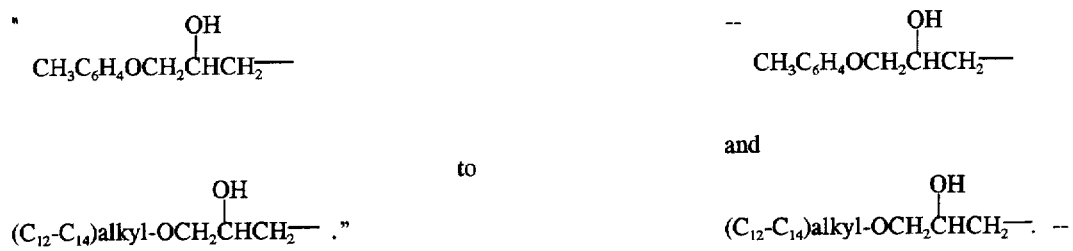

In column 6, at approximately line 32, under claim 6, please delete:

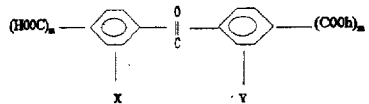

Signed and Sealed this

Seventh Day of November, 2000

Attest:

Q. TODD DICKINSON

*Attesting Officer*     *Director of Patents and Trademarks*